US00PP32885P2

(12) United States Plant Patent
Kobayashi

(10) Patent No.: US PP32,885 P2
(45) Date of Patent: Mar. 9, 2021

(54) POINSETTIA PLANT NAMED 'DOPOINPRES'

(50) Latin Name: ***Euphorbia pulcherrima* Willd.**
Varietal Denomination: Dopoinpres

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/873,894

(22) Filed: Aug. 4, 2020

(51) Int. Cl.
*A01H 5/02* (2018.01)
*A01H 6/38* (2018.01)

(52) U.S. Cl.
USPC ..... Plt./307
CPC ..... *A01H 6/385* (2018.05)

(58) Field of Classification Search
USPC ..... Plt./307
CPC ..... A01H 6/385
See application file for complete search history.

*Primary Examiner* — Anne Marie Grunberg
(74) *Attorney, Agent, or Firm* — C. Anne Whealy

(57) ABSTRACT

A new and distinct cultivar of *Poinsettia* plant named 'Dopoinpres', characterized by its uniform, upright and mounded plant habit; moderately vigorous growth habit; freely and upright branching habit; dark green-colored leaves; plants flower on or about November 18 in Southern California under natural season conditions; large inflorescences with dark red-colored flower bracts; and good post-production longevity.

1 Drawing Sheet

Botanical designation: *Euphorbia pulcherrima* Willd.
Cultivar denomination: 'DOPOINPRES'.

STATEMENT REGARDING PRIOR DISCLOSURES BY THE INVENTOR AND APPLICANT

The Inventor and Applicant assert that no sales, publications or advertisements relating to sales, offers for sale or public distribution occurred more than one year prior to the effective filing date of this application. Any information about the claimed plant would have been obtained from a direct or indirect disclosure from the Inventor and/or the Applicant. Inventor and Applicant claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Poinsettia* plant, botanically known as *Euphorbia pulcherrima* Willd., and hereinafter referred to by the cultivar name 'Dopoinpres'.

The new *Poinsettia* plant is a product of a planned breeding program conducted by the Inventor in Encinitas, Calif. The objective of the breeding program is to create new uniform *Poinsettia* plants having large inflorescences with attractive flower bracts and excellent post-production longevity.

The new *Poinsettia* plant is a naturally-occurring whole plant mutation of *Euphorbia pulcherrima* Willd. 'Eckadire', disclosed in U.S. Plant Pat. No. 12,846. The new *Poinsettia* plant was discovered and selected by the Inventor as a single flowering plant from within a population of plants of 'Eckadire' in a controlled greenhouse environment in Encinitas, Calif. on Jan. 11, 2002.

Asexual reproduction of the new *Poinsettia* plant by terminal vegetative cuttings in a controlled greenhouse environment in Encinitas, Calif. since April, 2002 has shown that the unique features of this new *Poinsettia* plant are stable and reproduced true to type in successive generations of asexual reproduction.

SUMMARY OF THE INVENTION

Plants of the new *Poinsettia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dopoinpres'. These characteristics in combination distinguish 'Dopoinpres' as a new and distinct *Poinsettia* plant:

1. Uniform, upright and mounded plant habit.
2. Moderately vigorous growth habit.
3. Freely and upright branching habit.
4. Dark green-colored leaves.
5. Under natural season conditions, plants flower on or about November 18 in Southern California.
6. Large inflorescences with dark red-colored flower bracts.
7. Good post-production longevity.

In side-by-side comparisons conducted in Encinitas, Calif., plants of the new *Poinsettia* differ primarily from plants of the mutation parent, 'Eckadire', in time to flower as plants of the new *Poinsettia* flower about 14 days earlier than plants of 'Eckadire' when grown under natural season conditions.

Plants of the new *Poinsettia* can be compared to plants of the *Euphorbia pulcherrima* Willd. 'Peterstar', disclosed in U.S. Plant Pat. No. 8,259. In side-by-side comparisons, plants of the new *Poinsettia* differ primarily from plants of 'Peterstar' in the following characteristics:

1. Leaves of plants of the new *Poinsettia* are darker green in color than leaves of plants of 'Peterstar'.
2. Plants of the new *Poinsettia* flower about one week earlier than plants of 'Peterstar' when grown under natural season conditions.
3. Plants of the new *Poinsettia* have dark red-colored flower bracts whereas plants of 'Peterstar' have bright red-colored flower bracts.

Plants of the new *Poinsettia* can also be compared to plants of the *Euphorbia pulcherrima* Willd. 'PER1295', disclosed in U.S. Plant Pat. No. 28,025. In side-by-side comparisons, plants of the new *Poinsettia* differ primarily from plants of 'PER1295' in the following characteristics:

1. Plants of the new *Poinsettia* are more vigorous than plants of 'PER1295'.
2. Leaves of plants of the new *Poinsettia* are not as dark green as leaves of plants of 'PER1295'.
3. Plants of the new *Poinsettia* have dark red-colored flower bracts whereas plants of 'PER1295' have crimson-colored flower bracts.

BRIEF DESCRIPTION OF THE PHOTOGRAPH

The accompanying photograph illustrates the overall appearance of the new *Poinsettia* plant showing the colors as true as it is reasonably possible to obtain in colored reproductions of this type. Colors in the photograph may differ slightly from the color values cited in the detailed botanical description which accurately describe the colors of the new *Poinsettia* plant. The photograph is a side perspective view of a typical flowering plant of 'Dopoinpres' grown in a container.

DETAILED BOTANICAL DESCRIPTION

Plants used in the aforementioned photograph and in the following detailed description were grown during the summer to late autumn in 16.5-cm containers in a polyethylene-covered greenhouse in Encinitas, Calif. under natural season conditions and cultural practices typical of commercial *Poinsettia* production. During the production of the plants, day temperatures averaged 24° C., night temperatures averaged 14° C. and light levels ranging from 3,500 to 4,500 foot-candles. Plants were pinched one time about four weeks after sticking rooted cuttings and were 23 weeks old when the photographs and the description were taken. Measurements and numerical values represent averages for typical flowering plants. In the following description, color references are made to The Royal Horticultural Society Colour Chart, 2015 Edition, except where general terms of ordinary dictionary significance are used.

Botanical classification: *Euphorbia pulcherrima* Willd. 'Dopoinpres'.

Parentage: Naturally-occurring whole plant mutation of *Euphorbia pulcherrima* Willd. 'Eckadire', disclosed in U.S. Plant Pat. No. 12,846.

Propagation:

*Type*.—Terminal vegetative cuttings.

*Time to initiate roots*.—About seven to ten days at night temperatures about 20° C. and day temperatures about 27° C.

*Time to produce a rooted young plant*.—About four weeks at night temperatures about 20° C. and day temperatures about 27° C.

*Root description*.—Fibrous; typically white in color, actual color of the roots is dependent on substrate composition, water quality, fertilizer type and formulation, substrate temperature and physiological age of roots.

Plant description:

*Plant and growth habit*.—Uniform, upright and mounded plant habit; inverted triangle; large inflorescences with numerous flower bracts positioned above the foliar plane; moderately vigorous growth habit.

*Plant height*.—About 34 cm.

*Plant diameter or spread*.—About 48 cm.

*Lateral branch description*.—Quantity: Freely branching habit, about six to seven lateral branches develop after pinching; upright branching habit. Length: About 25.5 cm. Diameter: About 8 mm. Internode length: About 1.5 cm to 2 cm. Strength: Strong. Aspect: About 30° from vertical. Texture: Smooth, glabrous. Luster: Moderately glossy. Color: Close to 146A.

*Leaf description*.—Arrangement: Alternate, simple. Length: About 12.5 cm. Width: About 11 cm. Shape: Ovate. Apex: Acuminate. Base: Obtuse with truncate tendencies. Margin: Mostly entire to occasionally irregularly lobed; slightly undulate. Aspect: Outwardly to slightly upright; keeled. Texture, upper and lower surfaces: Rugose, glabrous; prominent venation on lower surface. Luster, upper surface: Slightly glossy. Luster, lower surface: Matte. Venation pattern: Pinnate, arcuate. Color: Developing and fully expanded leaves, upper surface: Darker green than N189A; midvein, close to 146A and lateral venation, close to N189A. Developing and fully expanded leaves, lower surface: Close to 147A; midvein, distally, close to 146A to 146B and proximally, close to 146B overlain with close to 187A; lateral venation, close to 147A. Leaf petioles: Length: About 7.25 cm. Diameter: About 5 mm. Texture, upper and lower surfaces: Smooth, glabrous. Luster, upper and lower surfaces: Moderately glossy. Color, upper and lower surfaces: Close to 187A to 187B.

Inflorescence description:

*Inflorescence type and habit*.—Terminal inflorescences are compound corymbs of cyathia with numerous colored flower bracts subtending the cyathia; inflorescences uniformly positioned above the foliar plane.

*Fragrance*.—None detected.

*Flowering response*.—Under natural season conditions, plants typically flower on or about November 18 in Southern California; under artificial long nyctoperiod/short photoperiod conditions, plants flower about eight weeks later.

*Post-production longevity*.—Good post-production longevity; plants of the new *Poinsettia* maintain good substance and flower bract color for about four to six weeks under interior conditions; flower bracts persistent and cyathia not persistent.

*Inflorescence diameter*.—About 32 cm to 35 cm.

*Inflorescence height* (*depth*).—About 6 cm to 9 cm.

*Flower bracts*.—Quantity per inflorescence: Numerous, about 24 to 28. Length, largest bracts: About 15 cm. Width, largest bracts: About 10.5 cm. Shape: Ovate. Apex: Acuminate. Base: Obtuse with truncate tendencies. Margin: Entire; slightly undulate. Aspect: Mostly horizontal to slightly upright; keeled. Texture, upper and lower surfaces: Slightly rugose, glabrous; satiny; prominent venation on lower surface. Luster, upper and lower surfaces: Matte. Venation pattern: Pinnate, arcuate. Color: Developing or transitional bracts, upper surface: Ground color, darker green than 147A; irregular and random sectors, close to N45A. Developing or transitional bracts, lower surface: Ground color, close to 147B; irregular and random sectors, close to 45A to 45B. Fully expanded bracts, upper surface: Close to N45A. Fully expanded bracts, lower surface: Close to N45B to N45C. Bract petioles: Length: About 5.25 cm. Diameter: About 3 mm. Texture, upper and lower surfaces: Smooth, glabrous. Luster, upper and lower surfaces: Moderately glossy. Color, upper surface: Close to 185A. Color, lower surface: Close to 144A variably overlain with close to 185A.

*Cyathia*.—Quantity per corymb: About 16 to 18. Length: About 1 cm. Width: About 6 mm. Shape: Ovoid. Texture: Smooth, glabrous. Color, inner and outer surfaces: Close to 144A to 144B.

*Nectaries*.—Quantity per cyathium: One. Length: About 5.5 mm. Width: About 5 mm. Shape: Roughly deltoid. Texture: Smooth, glabrous. Color, inner and outer surfaces: Close to 13A.

*Peduncles*.—Length: About 5 mm. Diameter: About 2.5 mm. Strength: Strong. Aspect: Mostly upright to slightly outwardly. Texture: Smooth, glabrous. Color: Close to 144A to 144B.

*Reproductive organs*.—Stamens: Quantity per cyathium: About 15 to 20. Filament length: About 5 mm. Filament color: Close to 53A. Anther shape: Round to oval; bi-lobed. Anther length: Less than 1 mm. Anther color: Close to 12A. Amount of pollen: None observed. Pistils: Quantity per cyathium: One; tri-parted. Pistil length: About 7.5 mm. Stigma shape: Lanceolate, six-parted, recurved. Stigma color: Close to 59A. Style length: About 5 mm. Style color: Close to 59A. Ovary color: Close to 144A to 144B. Fruits & seeds: To date, fruit and seed development has not been observed on plants of the new *Poinsettia*.

Pathogen & pest resistance: To date, plants of the new *Poinsettia* have not been shown to be resistant to pathogens and pests common to *Poinsettia* plants.

Temperature tolerance: Plants of the new *Poinsettia* have been observed to tolerate temperatures ranging from about 16° C. to about 29° C.

It is claimed:

1. A new and distinct *Poinsettia* plant named 'Dopoinpres' as illustrated and described.

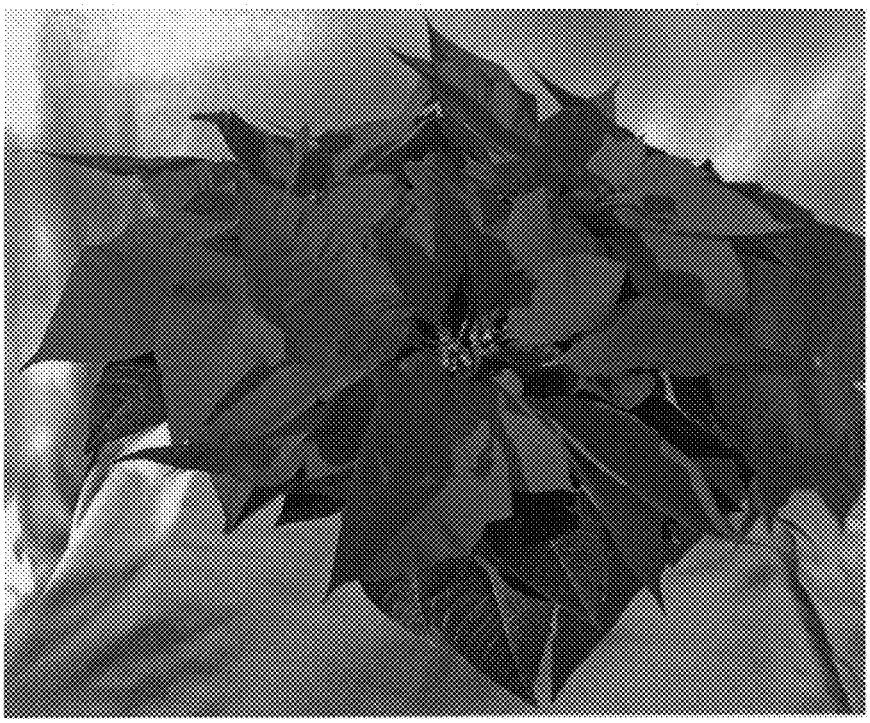

* * * * *